(12) United States Patent
Brovold

(10) Patent No.: US 7,107,858 B2
(45) Date of Patent: Sep. 19, 2006

(54) HOT MIX ASPHALT LOAD SIMULATOR

(75) Inventor: Thomas Emil Brovold, Minneapolis, MN (US)

(73) Assignee: Test Quip LLC, Barnes, WI (US)

( * ) Notice: Subject to any disclaimer, the term of this patent is extended or adjusted under 35 U.S.C. 154(b) by 0 days.

(21) Appl. No.: 10/880,803

(22) Filed: Jun. 30, 2004

(65) Prior Publication Data

US 2005/0011276 A1    Jan. 20, 2005

Related U.S. Application Data

(60) Provisional application No. 60/483,674, filed on Jun. 30, 2003.

(51) Int. Cl.
*G01N 3/00* (2006.01)
(52) U.S. Cl. ............................................... 73/818
(58) Field of Classification Search ................ 33/534; 73/818–825
See application file for complete search history.

(56) References Cited

U.S. PATENT DOCUMENTS

| 6,477,783 B1 | 11/2002 | Harman et al. |
| 6,729,189 B1 * | 5/2004 | Paakkinen .................... 73/824 |
| 6,889,558 B1 * | 5/2005 | Hines .......................... 73/825 |

* cited by examiner

*Primary Examiner*—Max Noori
(74) *Attorney, Agent, or Firm*—Oppenheimer Wolff & Donnelly LLP

(57) ABSTRACT

A device for simulating the various forces a load of hot asphalt mix places on the inside of a gyratory compactor allows the calibration of the compactor without requiring actual asphalt to be used. Obviating the need for asphalt during calibration significantly increases the accuracy of the calibration and provides an opportunity for more data to be obtained. The device is capable of being heated to hot asphalt temperatures for more accurate calibration.

29 Claims, 7 Drawing Sheets

HOT MIX ASPHALT LOAD SIMULATOR

REFERENCE TO RELATED APPLICATION

This application claims priority from provisional application 60/483,674 filed Jun. 30, 2003 and entitled HOT MIX ASPHALT LOAD SIMULATOR.

BACKGROUND OF THE INVENTION

The present invention relates to a device that can be used to simulate a hot asphalt load placed on an asphalt gyratory compactor dynamic angle validator (DAV).

Asphalt is a heterogeneous mixture of aggregate and asphalt binders and has attributes that can vary widely with factors such as aggregate size, binder quality, and air content. For example, if the air content of a batch of asphalt is too low, such as less than 4%, the asphalt starts to exhibit pressure transmission qualities similar to that of a liquid. Thus, forces placed upon the asphalt are transmitted through the asphalt, rather than through the aggregate structure, and can cause the asphalt to buckle. Considering the material and construction costs of building an asphalt roadway, it becomes easy to see how crucial it is to use accurate asphalt quality control equipment to ensure asphalt mixes meet minimum standards before they are applied to a roadway.

One widely used piece of quality control equipment is the gyratory compactor. Used to measure compaction and other composition characteristics, the gyratory compactor includes a cylindrical mold placed inside a compactor and filled with hot asphalt. A plate is placed above and below the hot asphalt in the mold, and a piston is used to compress one plate toward the other, thereby compressing the asphalt. In order to more accurately simulate the types of pressures that the asphalt will be subjected to when exposed to vehicle traffic, the cylindrical mold is tilted slightly and gyrated around a vertical axis while maintaining the tilt angle. Doing so allows the aggregate to shift and settle during compression.

Through exhaustive experimentation, it has been determined that the desired tilt angle is 1.25 degrees. For many years, gyratory compactors were calibrated by measuring the difference between the tilt angle of an outside wall of the mold in relation to a vertical axis, represented by an inside wall of the gyratory compactor. Later, it was determined that this simple measurement did not accurately represent the complexities of the angle of the force being placed on the asphalt sample. The plates placed above and below the asphalt sample transmit nearly all of the vertical compaction force to the asphalt. If these plates do not remain parallel to each other, and perpendicular to the vertical centerline of the gyratory compactor, the angle between the outside wall of the mold and the inside wall of the gyratory compactor (representing vertical) is not accurately related to the angle between the forces applied by the plates on the mix and the internal walls of the tilted mold.

The shortcomings of measuring the external angle of the mold as the sole indicator of tilt angle lead to the development of the Dynamic Angle Validator (DAV), shown and described in U.S. Pat. No. 6,477,783 and incorporated by reference herein. The DAV is an angle measurement device that measures the angle between one of the two plates acting on the asphalt and an internal wall of the mold. Due to the positioning of the DAV on the plate during measurements, deflections of the plates are accounted for in the measurement of the angle.

In order to accurately measure the reaction of mold and plates to the compression of hot asphalt, it has been heretofore required that hot asphalt be used in conjunction with the DAV during calibration. However, using a DAV with hot asphalt presents problems and challenges. Asphalt varies widely in its composition. Thus, each batch of hot asphalt is going to transmit different forces on the inside walls of the mold, and on the plates. Thus, calibrating a gyratory compactor using hot asphalt becomes a less-than-precise method of performing a calibration, which is by its nature supposed to be a very accurate exercise. The heat of the asphalt presents DAV design challenges. Prior to compaction, the asphalt, mold, and plates are heated to 300 F, just as the asphalt mixture is when produced at the plant to allow the asphalt to shift during compaction and to prevent the asphalt from solidifying in the mold. The DAV must therefore be able to operate in a 300 F environment and under approximately 600 kpa of compaction force. Some DAV designs are able to operate in these environments, while others have electronics that fail at elevated temperatures.

Calibrating a gyratory compactor with asphalt is also very time consuming. When placed in the mold, the hot mix is completely loose. The mix must be compacted for three minutes while readings are taken on the internal tilt angle. Considering that a calibration requires two runs for each sample (one where the DAV is placed at the top of the mold and one where the DAV is placed at the bottom of the mold) and at least two samples are used so that data can be interpolated or extrapolated linearly, a minimum of four three minute runs, plus data retrieval and DAV cooling time, is necessary with each calibration.

Another problem with calibrating a gyratory compactor with hot mix asphalt is that the height of the asphalt column greatly affects the forces placed on the mold by the asphalt. The greater the height, the greater the moment that results from the angle of the compaction force relative to the mold. Gyratory compactors are designed to test 115 mm columns of asphalt. Thus, in order to calibrate a compactor with asphalt, the DAV and 115 mm of asphalt must be placed in the mold. However, most compactors are not tall enough to accommodate the added height of the DAV. Thus, accurate measurements cannot be obtained. Rather, a smaller column of asphalt is placed in the mold and the data is extrapolated. This method may not be as accurate as using a 115 mm column of asphalt.

It is evident that there is a significant need for a device that accurately replicates the loads placed on the inside walls of a mold, as well as on the upper and lower plates, when hot asphalt is compacted in a gyratory compactor. Preferably, this device could be used in a hot or cold environment, and with a variety of different DAV designs.

There is further a need for a device designed with at least one variable that can be selected to simulate different types of asphalt mixes.

There is also a need for a device that accurately replicates the loads placed on the inside walls of a mold by a 150 mm column of hot asphalt, yet short enough to fit in most molds with most DAVs.

BRIEF SUMMARY OF THE INVENTION

The present invention meets the aforementioned needs by providing a device and method that applies the same forces and moments on a mold as a hot asphalt mixture would during compaction. The device includes two pieces that act against each other during compaction.

The first piece has a base surface that contacts the DAV and includes a feature, such as a ridge, détente, or other contour that is configured to mate with a corresponding feature on the DAV. These mating features keep the first piece from moving relative to the DAV. The first piece also has an active surface that is either angled relative to the first surface or convexly curved.

The second piece has a first surface and a second surface. The first surface acts against the active surface of the first piece. The second surface contacts an end surface of the gyratory compactor, such as an end plate or piston.

The second piece is not connected to the first piece. Further, the first surface of the second piece is angled relative to the second surface of the second piece. The first and second pieces are constructed and arranged such that, when they are arranged for use in the gyratory compactor, but prior to being subjected to compaction forces, the contact area between the active surface of the first piece and the first surface of the second piece takes the shape of a complete circle. However, once the compaction forces are applied in combination with the forces necessary to tilt the mold, the first and second pieces maintain their angles relative to each other, but become laterally offset by the tilting forces on the mold. Becoming laterally offset while maintaining their original, no-load angles causes the second piece to "ride up" the first piece, thereby reducing the contact area to a single point. The forces applied through this single point are representative of a column of hot asphalt and are precisely repeatable. These forces are also dependent on the angled first surface of the second piece. By changing the angle of this first surface, a different type of asphalt can be simulated.

These two pieces have a combined height that is less than that of a column of asphalt, and are therefore useable with any gyratory compactor and DAV. Additionally, with some gyratory compactor/DAV combinations, there is enough room to place a DAV, the two-piece load simulator, and a column of asphalt.

DETAILED DESCRIPTION OF THE INVENTION

The Components

Figure 1:
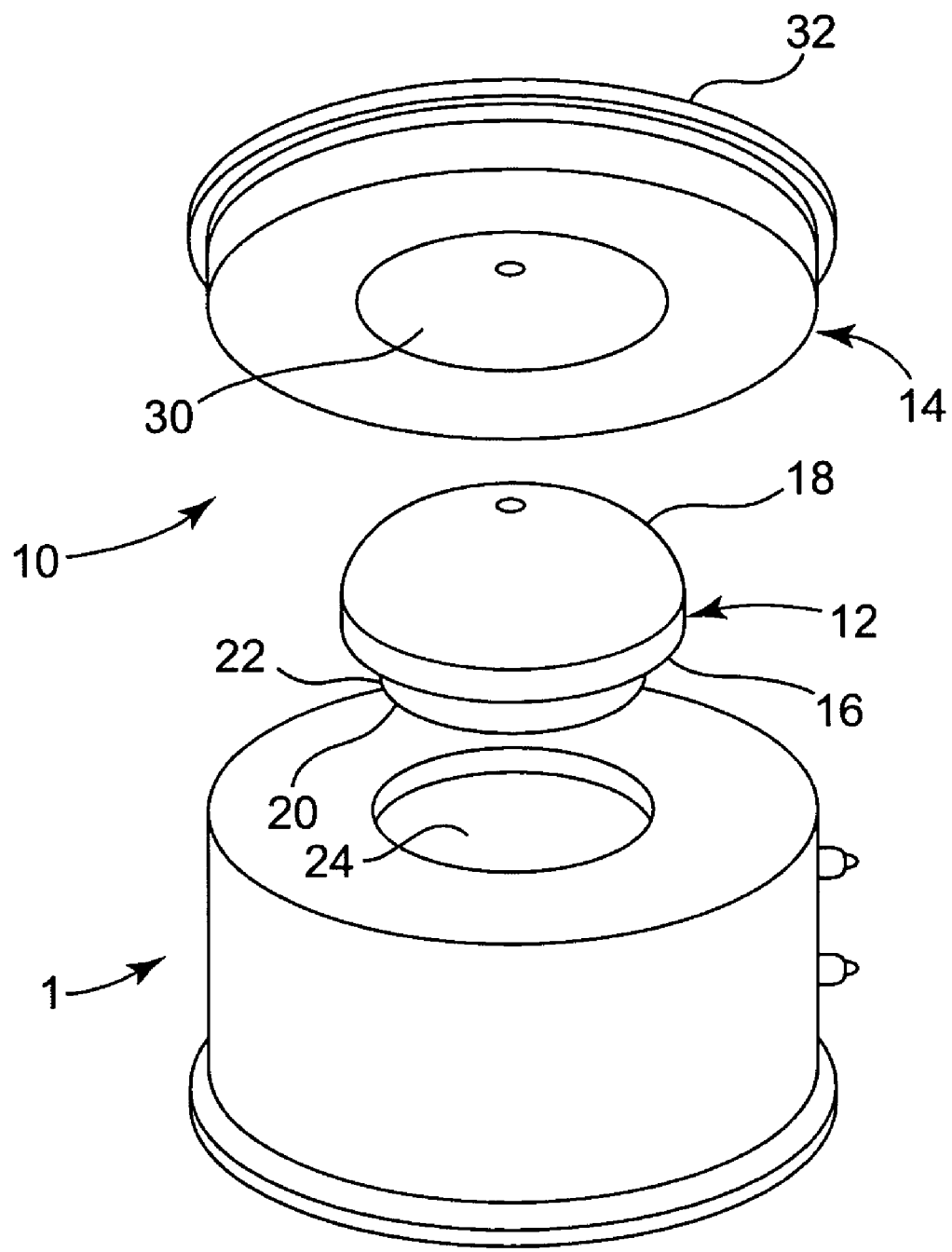
FIG. 1 is an exploded perspective view of an embodiment of the present invention.
Figure 2:
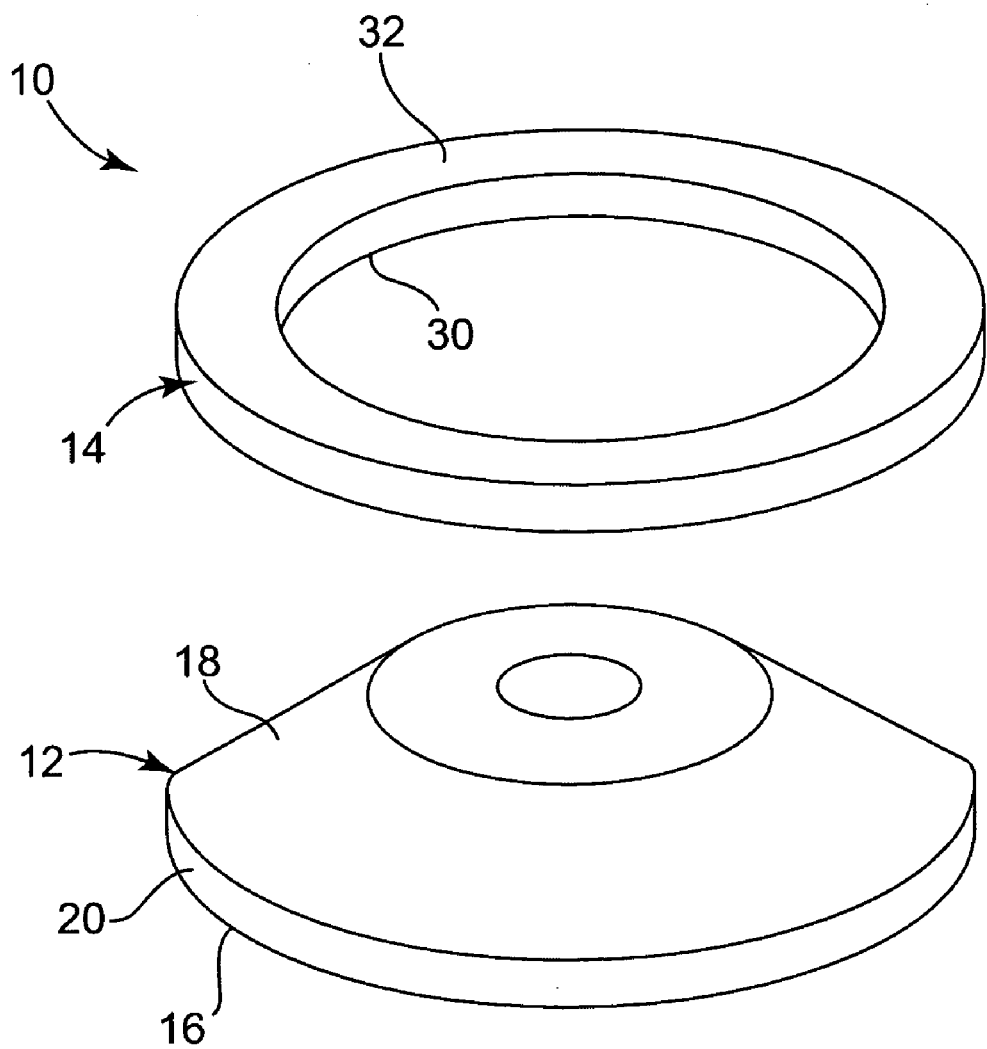
FIG. 2 is an exploded perspective view of an embodiment of the present invention.

Referring now to the Figures and first to FIGS. 1 and 2, two embodiments of a hot mix asphalt load simulator 10 of the present invention are shown. The simulator 10 includes a first piece 12 and a second piece 14. The first piece 12 has a base surface 16 and an active surface 18. The base surface 16 includes a feature 20 that is useable to anchor the first piece 12 to a DAV 1. The particular feature 20 shown in FIG. 1 includes a circular ledge 22 that fits into an indentation 24 in the top of the DAV 1. The feature 20 of the embodiment of FIG. 2 is a diameter that is sized to fit within the indentation 24 (FIG. 1) in the top of the DAV 1. One skilled in the art will realize that there are numerous acceptable substations for the feature 20 shown in FIG. 1. A circular ledge 22 is provided in FIG. 1 as a best mode for purposes of manufacturing ease. However, the purpose of feature 20 is to prevent the first piece 12 from sliding on the DAV 1 and any configuration accomplishing this function would be acceptable. The active surface 18 is opposite the base surface 16 and has a circular cross section along a horizontal plane such as a conical surface or a spherical surface. The active surface 18 of the simulator 10 of FIG. 1 is spherical. The active surface 18 of the simulator 10 of FIG. 2 is conical.

The second piece 14 has a first surface 30 and a second surface 32. The first surface 30 is angled relative to the second surface 32, which acts, directly or indirectly, against an end of the gyratory compactor. The first surface 30 is constructed and arranged to act against the active surface 18 of the first piece 12. The second piece 14 of FIG. 1 is a disk-shaped piece while the second piece 14 of FIG. 2 is ring-shaped.

The first and second pieces 12 and 14 of the device 10 are of sturdy construction; able to withstand the pressures and heat of a gyratory compactor. Preferably, the pieces 12 and 14 are constructed of stainless steel and are substantially solid.

Figure 3:
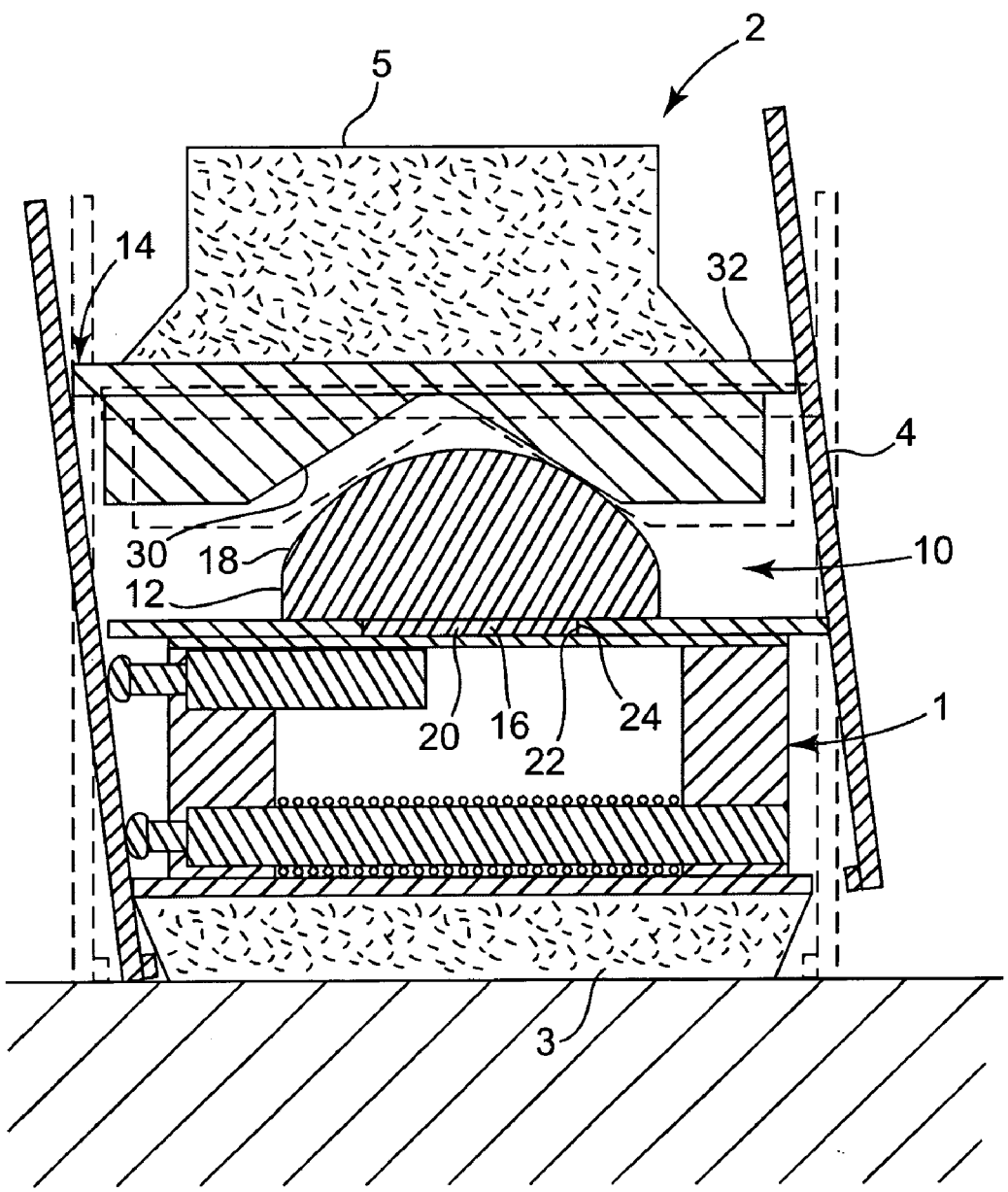
FIG. 3 is a cutaway elevation of an embodiment of the present invention being used in a gyratory compactor with a DAV.

Referring now to FIG. 3, the device 10 is shown being used with a DAV 1 in a gyratory compactor 2. The DAV 1 rests on an end plate 3 of the compactor 2 within the cylindrical mold 4. The first piece 12 of the device 10 is placed on the DAV 1 in such a manner that the feature 20 of the base surface 16 mates with the corresponding feature (indentation 24, in this case) of the DAV 1.

The second piece 14 of the device 10 is placed on the first piece 12 such that the active surface 16 of the first piece 12 is received by the first surface 30 of the second piece 14. A moveable piston or ram 5 of the compactor 2 provides pressure against the second surface 32 of the second piece 14. The ram 5 may directly contact the second piece 14 or a plate (not shown) may be interposed between the ram 5 and the second piece 14. Pressure from the ram 5 keeps the second surface 32 parallel to the DAV 1.

Movement Between the First and Second Pieces

Once the gyratory compactor 2 is started, the mold 4 is tilted and presses against the second piece 14. This causes the second piece 14 to ride up the first piece 12 as the second piece 14 becomes laterally offset from the first piece 12. This action is shown in FIG. 2 by comparing the original, pre-tilt positions of the second piece 14 and the mold 4, drawn in phantom lines, to the tilted positions. The second piece 14 is offset from its original position both laterally and vertically.

Figure 4:
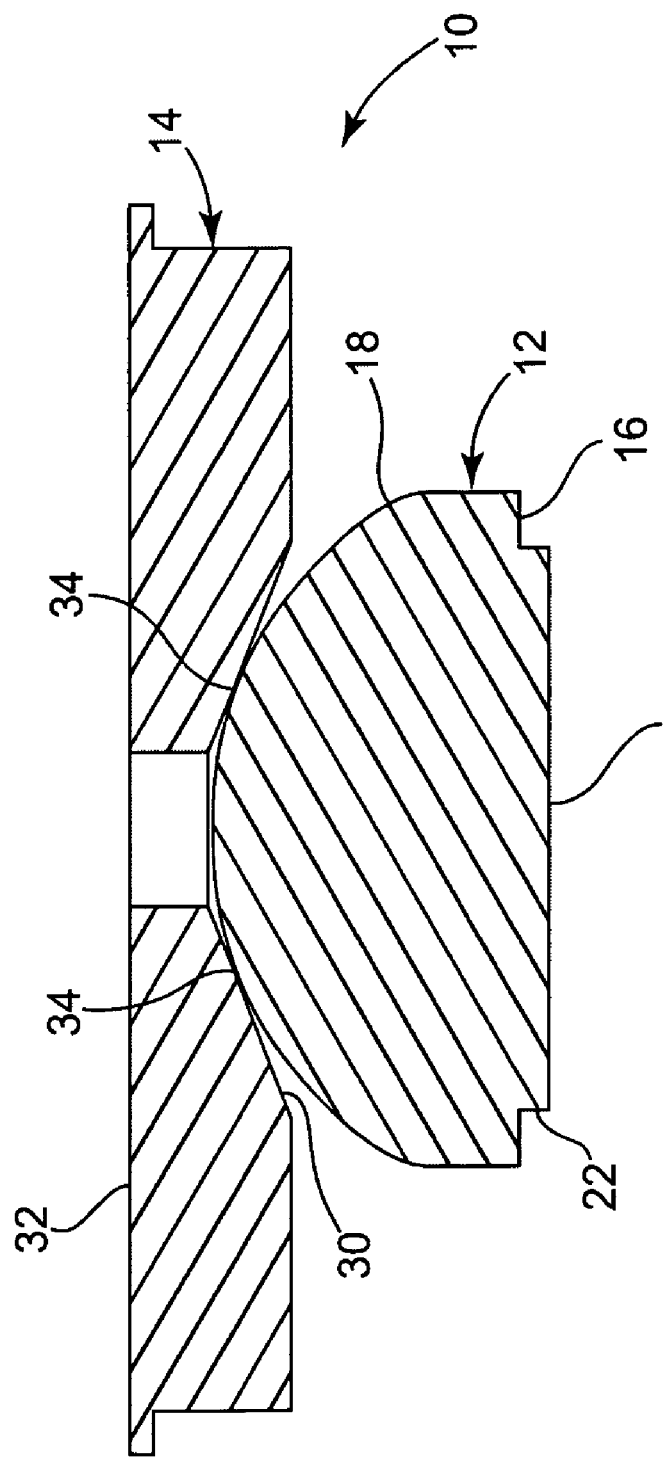
FIG. 4 is a cutaway elevation of an embodiment of the present invention prior to tilting.
Figure 5:
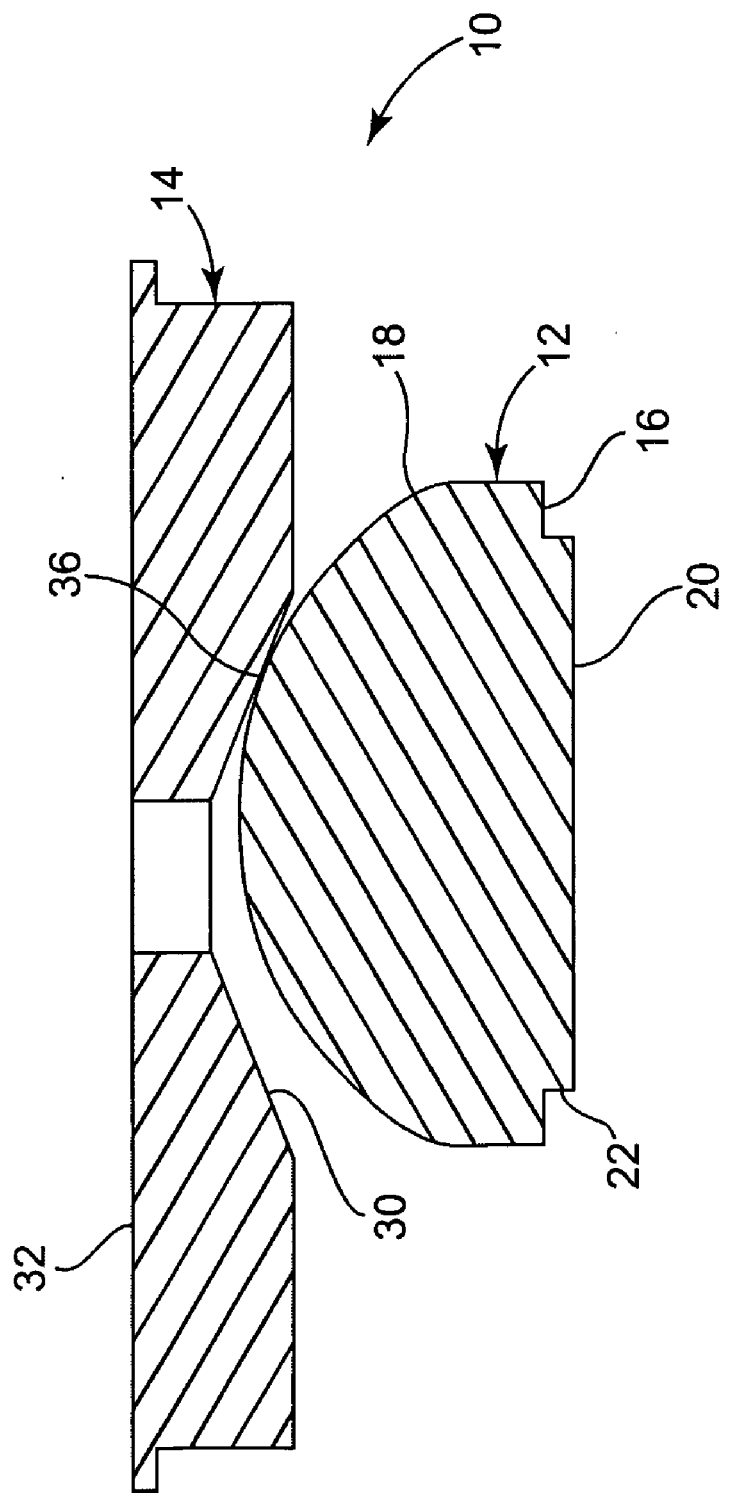
FIG. 5 is a cutaway elevation an embodiment of the present invention after tilting.

FIGS. 4 and 5 provide a more detailed view of this offset. In FIG. 4, the second piece 14 has not been offset. The second piece 14 rests on top of the active surface 18 of the first piece 12 such that the second piece 14 is centered on the first piece 12. The first surface 30 of the second piece 14 contacts the active surface 18 of the first piece 12 in such a manner as to form circular ring of contact points 34. In FIG. 5, the mold (not shown) has been tilted, causing the second piece 14 to shift laterally and upwardly, thereby reducing the ring of contact points to a single point 36.

The Forces Imparted by the Simulator

Having described the physical features of the device 10, and the relative movement of the pieces 12 and 14 when the mold 4 is tilted, discussion will now turn to the forces imparted on the DAV 1 and the compactor 2 by the device during operation and how these forces closely simulate a load of hot mix asphalt.

Figure 6:
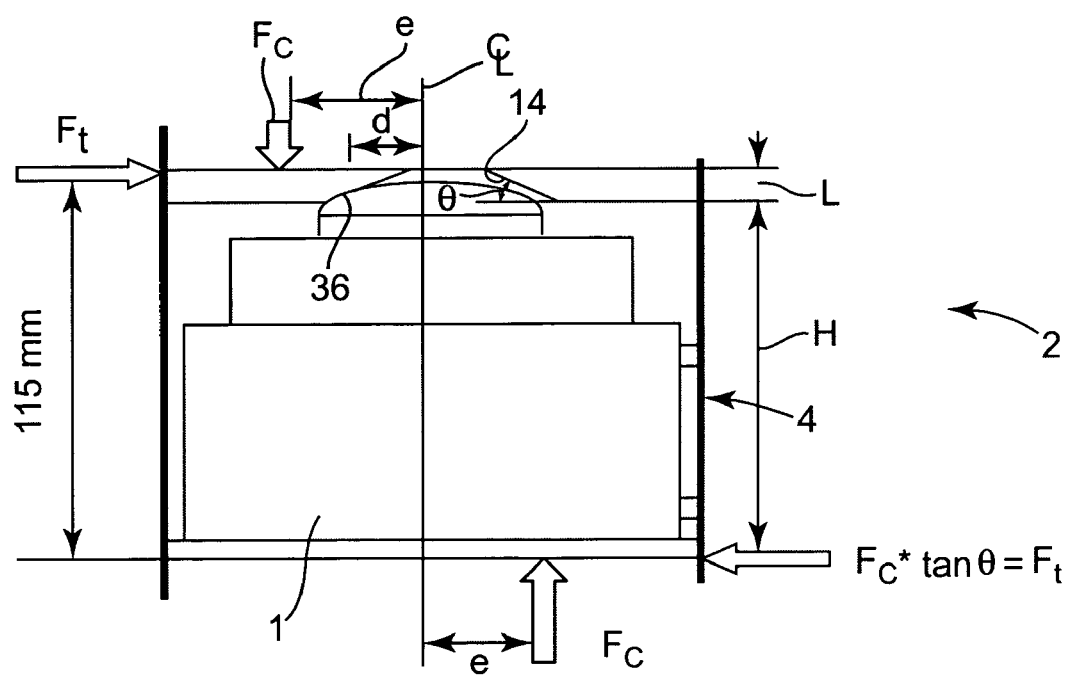
FIG. 6 is a diagram showing some of the forces acting on a DAV, a mold, and the device of the present invention; and, FIG. 7 is a diagram showing some of the forces acting on a piece of the present invention.

FIG. 6 shows the various forces at play during a calibration of a gyratory compactor 2. The two external forces that act on the simulator 10 and the DAV 1 are the resultant force $F_c$ from the compression of the ram or piston of the gyrator compactor, and the resultant tilting force $F_t$ placed on the outside of the mold 4 by the compactor.

Prior to the application of $F_t$, $F_c$ falls on the centerline ℄ of the mold and DAV 1. When $F_t$ is applied, the contact point 36 moves laterally a distance d. This shifts $F_c$ to provide a countering moment as the mold 4 tilts and equilibrium is achieved. The angle θ between the first surface 30 of the second piece 14 and horizontal is determinative of the distance e to which the force $F_c$ will shift from ℄, and thus, the size of the resulting moment. (If using the device 10 of FIG. 2, the angle θ is measured from horizontal to the active surface 18 of the first piece 12.) The moment $M_{cDAV}$ on the DAV 1 due to the compressive force $F_c$ of the ram can be represented by:

$$M_{cDAV} = F_c \cdot d + F_c \cdot e$$

The relationship between $F_t$ and $F_c$ at equilibrium is dependent on θ as follows:

$$F_t = F_c \tan \theta$$

This relationship is due to the shifting of the force $F_c$ from the centerline ℄ to the angled first surface 30. The vertical compressive force $F_c$, applied against the angled first surface 30, results in a lateral force $F_L$ that is equal and opposite to the tilting force $F_t$.

The moment $M_{LDAV}$ on the DAV 1 created by the lateral force $F_L$ counteracts the moment $M_{cDAV}$ created by the eccentric compressive force $F_c$, and can be represented by:

$$M_{LDAV} = F_L \cdot H = F_c \cdot d + F_c \cdot e$$

Figure 7:
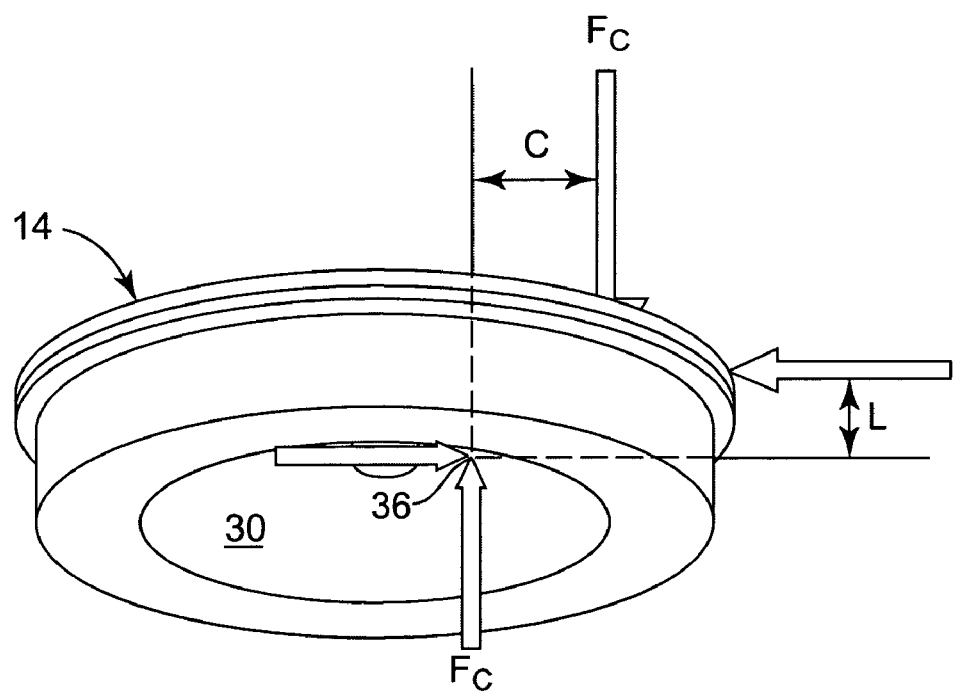

FIG. 7 shows the balance of the moments on the second piece 14. Again, $F_c$ is the compressive force from the ram of the gyratory compactor 2. Similarly, $F_L$ is the lateral component of $F_c$ resulting from the angled first surface 30 and is related to Fc as follows:

$$F_L = F_c \tan \theta$$

The moments created by the forces $F_c$ and $F_L$ are dependent on the location of the contact point 36 on the first surface 30 of the second piece 14. $F_c$ creates a moment $M_{c2nd}$ in one direction due to the offset horizontal distance c between the contact point 36 and the resultant force vector $F_c$. This moment $M_{c2nd}$ is calculated:

$$M_{c2nd} = F_c \cdot c$$

The countering moment is created by the lateral component force $F_L$ and the vertical distance L between the contact point 36 and the force vector $F_L$. This moment $M_{L2nd}$ is calculated:

$$M_{L2nd} = F_L \cdot L$$

Referring again to FIG. 6, a distance H can be defined as the height of the contact point 36 above the base of the DAV 1. Because the gyratory compactor 2 is calibrated to measure a column of asphalt 115 mm tall, it is desired that the height of the DAV 1 and the device 10 equal 115 mm. Thus:

$$L + H = 115 \text{ mm}$$

The moment $M_t$ on the mold 4 due to the tilting force $F_t$ is thus:

$$M_t = F_t(L+H) = F_t \cdot 115 \text{ mm} = F_c \tan \theta \cdot 115 \text{ mm}$$

The countering moment $M_c$ on the DAV 1 and device 10 is:

$$M_c = F_c \cdot e$$

The distance e, between the resultant compressive force $F_c$ and the centerline ℄ can be determined using:

$$e = \tan \theta \cdot 115 \text{ mm}/2$$

Realizing the relationships between the distances c, d and e are as follows:

$$d + c = e$$

allows the following substitutions and reductions to be made in order to derive an alternative formula for e:

$$F_c \tan\theta \cdot H = F_c \cdot d + F_c \cdot e \Rightarrow \tan\theta \cdot H = d + e \Rightarrow \tan\theta = \frac{d+e}{H}$$

$$F_c \tan\theta \cdot L = F_c \cdot c \Rightarrow \tan\theta \cdot L = c \Rightarrow \tan\theta = \frac{c}{L}$$

$$\frac{d+e}{H} = \frac{c}{L} = \frac{e-d}{L}$$

$$\left(\frac{d+e}{H}\right)L = e - d \Rightarrow \frac{dL}{H} + \frac{eL}{H} = e - d$$

$$\frac{dL}{H} + d = e - \frac{eL}{H} \Rightarrow d\left(\frac{L}{H} + 1\right) = e\left(1 - \frac{L}{H}\right)$$

$$e = d\left(\frac{1 + \frac{L}{H}}{1 - \frac{L}{H}}\right)$$

Practical Use of Mathematical Relationships

Knowledge of the aforementioned mathematical relationships allows the device 10 to be used to perform tests previously unavailable. For example, the angle θ of the first surface 30 of the second piece 14 is used to simulate the shear force normally created by an asphalt mix. Changing the angle θ, in other words using a variety of second pieces 14 each having a different angle θ, allows a determination of how a particular gyratory compactor will react to varying asphalt loads.

Furthermore, the device 10 can be used in a quality control capacity for various asphalt mixes. For example, if an asphalt mix is purported to have a shear characteristic that corresponds to a particular angle θ on the simulator device 10, a run can be made with the DAV 1 and the simulator 10 to determine the corresponding reaction of the mold 4 and the end plates 3 of the compactor 2. Then, the simulator may be removed and a load of the asphalt can be placed in the mold 4 with the DAV 1. After the run, the data from the loaded run should match the data from the simulated run. Furthermore, because the angle θ has a known mathematical relationship to the forces created by the simulator, measuring the angle θ with an asphalt load allows the quantification of the moments created by the asphalt.

It is contemplated that features disclosed in this application can be mixed and matched to suit particular circumstances. Various other modifications and changes will be apparent to those of ordinary skill in the art without departing from the spirit and scope of the present invention. Accordingly, reference should be made to the claims to determine the scope of the present invention.

What is claimed is:

1. A device for simulating forces exerted by hot asphalt on interior walls of mold in a gyratory compactor during operation without the use of a hot asphalt specimen, the device for use with a dynamic angle validator (DAV) within the mold of the gyratory compactor, the device comprising:
   a first piece having:
      a first means for preventing relative lateral motion between the DAV and the first piece;
      a second means for deflecting an object upwardly if the object is moved laterally in contact with and relative to the second means;
   a second piece having:
      a third means for contacting the second means of the first piece;
      a fourth means for maintaining a horizontal orientation while being moved laterally;
   whereby:
      the second piece is in contact with but not connected to the first piece or the gyratory compactor; and
      when the mold is tilted, the second piece shifts upwardly and laterally relative to the first piece, thereby exerting a lateral force on the mold and an upward force on an end of the gyratory compactor.

2. The device of claim 1 wherein the fourth means for maintaining a horizontal orientation while being moved laterally comprises a relatively horizontal surface.

3. The device of claim 1 wherein the first means for preventing relative lateral motion between the DAV and the first piece comprises a contour on the first piece that is configured to mate with a corresponding contour on the DAV.

4. The device of claim 3 wherein the contour on the first piece comprises a circular ledge.

5. The device of claim 1 wherein the second means for deflecting an object upwardly comprises an angled surface.

6. The device of claim 1 wherein the second means for deflecting an object upwardly comprises a convex surface.

7. The device of claim 1 wherein the second means for deflecting an object upwardly comprises a spherical surface.

8. The device of claim 1 wherein the third means for contacting the second means comprises an surface shaped like an inside surface of a portion of a cone.

9. The device of claim 1 wherein the third means for contacting the second means comprises an inside surface of a ring.

10. A method of simulating forces exerted by asphalt on an inside wall of a mold within a gyratory compactor without using an asphalt specimen, comprising:
   placing a first object in the mold, the first object having an active surface with a circular cross-section;
   placing a second object in the mold in operable contact with the active surface;
   applying a compacting force on at least one of the first and second objects;
   tilting the mold without tilting the compacting force, thereby causing the second object to ride up the active surface and create a lateral force between the first and second object that is representative of the forces exerted by asphalt when compacted in the gyratory compactor.

11. The method of claim 10 wherein applying a compacting force on at least one of the first and second objects comprises applying a compacting force directly on at least one of the first and second objects.

12. The method of claim 10 wherein placing a first object in the mold, the first object having an active surface with a circular cross-section comprises placing a first object in the mold, the first object having an active surface that is a section of a sphere.

13. The method of claim 10 wherein placing a first object in the mold, the first object having an active surface with a circular cross-section comprises placing a first object in the mold, the first object having an active surface that is a section of a cone.

14. The method of claim 10 wherein placing a second object in the mold in operable contact with the active surface comprises placing a first surface of the second object in operable contact with the active surface, the first surface having the shape of an inside portion of a cone.

15. The method of claim 10 wherein placing a second object in the mold in operable contact with the active surface comprises placing a ring-shaped object over the active surface of the first object.

16. The method of claim 10 wherein applying a compacting force on at least one of the first and second objects comprises applying a compacting force on the first object.

17. The method of claim 10 wherein applying a compacting force on at least one of the first and second objects comprises applying a compacting force on the second object.

18. The method of claim 10 wherein applying a compacting force on at least one of the first and second objects comprises applying a compacting force on both the first and second objects.

19. A device for simulating forces exerted by hot asphalt during operation of a gyratory compactor mold during operation, the device for use with a dynamic angle validator (DAV), the device comprising:
   a first piece having:
      a base surface for contacting the DAV and including a feature useable to prevent relative motion between the DAV and the first piece;
      an active surface;
   a second piece having:
      a first surface for contacting the active surface of the first piece;
      a second surface for contacting an end surface of the gyratory compactor;
   whereby:
      the second piece is not connected to the end surface of the gyratory compactor or the first piece;
      an angle formed between the first surface of the second piece and a horizontal line is greater than zero degrees and less than ninety degrees such that when a substantially vertical force is placed on the second piece, the first surface of the second piece acts against the active surface of the first piece and a lateral force is generated, thereby causing the second piece to ride up the first piece and reducing a contact area between the first and second pieces to substantially a single point.

20. The device of claim 19 wherein the active surface of the first piece comprises a portion of a sphere.

21. The device of claim 19 wherein the feature included on the base surface of the first piece is configured to mate with a corresponding feature on the DAV.

22. The device of claim 19 wherein the active surface of the first piece comprises a portion of a cone.

23. The device of claim 19 wherein the second piece comprises a disk.

24. The device of claim 19 wherein the second piece comprises a ring.

25. The device of claim 19 wherein the feature included on the base surface of the first piece comprises a circular ledge.

26. A load simulation device for use along with a dynamic angle validator with a gyratory compactor to simulate the loads placed on a compactor mold during operation without the use of an asphalt specimen, the load simulation device comprising:
 a base member for placement within the mold, the base member having a base surface and an active surface, the base surface being substantially planar while the active surface has a predefined contour;
 a translatable member having a planar surface and a contoured surface, the translatable member also for placement within the mold such that the contoured surface is in cooperating contact with the active surface of the base member, the contoured surface and the active surface configured such that a compressive force between the base surface and the planar surface of the translatable member along with a tilting of the mold causes a lateral translation of the translatable member creating lateral forces on the mold.

27. The load simulation device of claim 26 wherein the active surface is spherical and the contoured surface is conical.

28. The load simulation device of claim 26 wherein the active surface is conical and the contoured surface includes a raised ring.

29. The load simulation device of claim 26 wherein the base surface of the base member is in interlocking contact with an upper surface of the dynamic angle validator thus preventing any movement between the base member and the dynamic angle validator.

* * * * *